US006737557B2

(12) United States Patent
Cheung et al.

(10) Patent No.: US 6,737,557 B2
(45) Date of Patent: May 18, 2004

(54) HYDROCARBON UPGRADING PROCESS

(75) Inventors: Tin-Tack Peter Cheung, Bartlesville, OK (US); Steven A. Owen, Bartlesville, OK (US); Marvin M. Johnson, Bartlesville, OK (US); Mark E. Lashier, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/801,558

(22) Filed: Mar. 8, 2001

(65) Prior Publication Data
US 2004/0049093 A1 Mar. 11, 2004

Related U.S. Application Data

(62) Division of application No. 09/410,516, filed on Sep. 30, 1999, now Pat. No. 6,258,989.
(51) Int. Cl.[7] .............................. C07C 7/09; C07C 7/00
(52) U.S. Cl. .................. 585/809; 585/810; 208/347; 208/350; 203/17
(58) Field of Search .................. 585/809, 810; 208/347, 350, 354; 203/71

(56) References Cited

U.S. PATENT DOCUMENTS

| 3,492,220 A | * | 1/1970 | Lempert et al. ............ 208/144 |
| 4,450,069 A | * | 5/1984 | Kidwell et al. ............. 208/255 |
| 5,321,177 A | * | 6/1994 | Nakamura et al. .......... 585/318 |
| 5,401,890 A | * | 3/1995 | Parks ........................ 570/211 |
| 5,510,550 A | * | 4/1996 | Cheung et al. ............. 585/259 |
| 5,659,107 A | * | 8/1997 | Cheung et al. ............. 585/824 |
| 5,866,735 A | * | 2/1999 | Cheung et al. ............. 585/273 |

* cited by examiner

Primary Examiner—Thuan D. Dang
(74) Attorney, Agent, or Firm—Conley Rose, P.C.; Rodney B. Carroll; K. KaRan Reed

(57) ABSTRACT

A process for recovering DCPD from a hydrocarbon feedstock comprising introducing the hydrocarbon feedstock to a first column, recovering an overhead stream from the first column comprising $C_9-$ hydrocarbons, recovering a bottom stream from the first column comprising $C_{10}+$ hydrocarbons, feeding the bottom stream from the first column to a second column, recovering an overhead stream from the second column comprising DCPD, and recovering a bottom stream from the second column comprising fuel oil, wherein the two columns are sized and operated at defined conditions such as pressures, temperatures, reflux rates, and reboil rates.

17 Claims, No Drawings

HYDROCARBON UPGRADING PROCESS

This application is a division of application Ser. No. 09/410,516 filed Sep. 30, 1999, now U.S. Pat. No. 6,258,989.

The present invention relates to the field of hydrocarbon upgrading processes. More specifically, the present invention relates to the upgrading of a pyrolysis gasoline, obtained from a hydrocarbon thermal cracking process, to products such as $C_5$ diolefins, $C_5$ olefins, dicyclopentadiene, and aromatics such as benzene, toluene and xylene (BTX).

BACKGROUND OF THE INVENTION

It is well known in the art that processes for thermal cracking of hydrocarbons such as ethane, propane, naphtha, and the like, produce a by-product referred to as pyrolysis gasoline or aromatic concentrate, which can be debutanized to form debutanized aromatic concentrate (DAC). This pyrolysis gasoline or DAC typically contains $C_5$ and heavier hydrocarbons, such as $C_5$ diolefins, $C_5$ olefins, aromatics, cyclopentadiene (CPD), and dicyclopentadiene (DCPD).

It is desirable to convert the CPD to DCPD which is a valuable industrial chemical which can be used in the production of elastomers and unsaturated polyester resins.

Typical pyrolysis gasoline upgrading processes separate the pyrolysis gasoline into a $C_5$ stream containing CPD and a $C_6$+stream. The $C_5$ stream is then dimerized to form DCPD which is purified downstream. One problem with this process is that when the pyrolysis gasoline is obtained from storage, wherein a portion of the CPD is converted to DCPD, the separation of the pyrolysis gasoline into a $C_5$ stream and a $C_6$+stream, and dimerization of CPD in the $C_5$ stream to DCPD, will result in splitting the DCPD between the $C_5$ stream and the $C_6$+stream, necessitating the added expense of recovering DCPD from both the $C_5$ stream and the $C_6$+stream.

Therefore, development of a process capable of efficiently upgrading a pyrolysis gasoline, obtained either directly from a hydrocarbon thermal cracking unit or from storage, would be a significant contribution to the art.

SUMMARY OF THE INVENTION

It is an object of the present invention to provide a novel process for upgrading a hydrocarbon feedstock comprising $C_5$ olefins, $C_5$ diolefins, CPD, DCPD and aromatics to produce a DCPD product and/or a $C_5$ diolefin product and/or a $C_5$ olefin product and/or an aromatic product.

It is yet another object of the present invention to provide a novel process of increased efficiency for recovering DCPD from pyrolysis gasoline.

It is still another object of the present invention to provide a novel process of increased efficiency for producing and recovering DCPD from pyrolysis gasoline containing a significant quantity of DCPD.

It is yet another object of the present invention to provide a novel process of increased efficiency for recovering DCPD from pyrolysis gasoline wherein the DCPD has a Pt/Co color number below about 30.

In accordance with a first embodiment of the present invention, a process for upgrading hydrocarbons is provided including the steps of:

a) heating a hydrocarbon feedstock comprising CPD, DCPD, $C_5$ diolefins, benzene, toluene, and xylene in a heating zone, to dimerize CPD to DCPD, thereby forming a first effluent;

b) separating the first effluent into a $C_6$+stream and a $C_5$ diolefin stream comprising $C_5$ diolefins;

c) separating the $C_6$+stream into a $C_6$–$C_9$ stream and a $C_6$+stream;

d) separating the $C_{10}$+stream into a fuel oil stream and a DCPD stream comprising DCPD; and e) hydrotreating the $C_6$–$C_9$ stream to thereby form a BTX stream comprising benzene, toluene and xylene.

In accordance with a second embodiment of the present invention, a process for upgrading hydrocarbons is provided including the steps of:

a) heating a hydrocarbon feedstock comprising CPD, DCPD, $C_5$ diolefins, benzene, toluene, and xylene in a heating zone, to dimerize CPD to DCPD, thereby forming a first effluent;

b) separating the first effluent into a $C_5$–$C_9$ stream and a $C_{10}$+stream;

c) separating the $C_{10}$+stream into a fuel oil stream and a DCPD stream comprising DCPD;

d) contacting the $C_5$–$C_9$ stream with a selective hydrogenation catalyst, in a first reaction zone and in the presence of hydrogen, to hydrogenate at least a portion of the diolefins, alkynes, and styrene contained in the $C_5$–$C_9$ stream, thereby forming a second effluent;

e) separating the second effluent into a $C_6$–$C_9$ stream and a $C_5$ olefin stream comprising $C_5$ olefins;

f) contacting the $C_6$–$C_9$ stream with a hydrodesulfurization catalyst, in a second reaction zone and in the presence of hydrogen, to desulfurize at least a portion of the sulfur-containing compounds contained in the $C_6$–$C_9$ stream thereby forming a BTX stream comprising benzene, toluene and xylene.

In accordance with a third embodiment of the present invention, a process for recovering DCPD from a hydrocarbon feedstock is provided including the steps of:

a) providing a first separation column, a first overhead condenser, and a first reboiler, the first separation column defining a first separation zone having an upper portion, a lower portion and an intermediate portion, the intermediate portion of the first separation zone comprising at least about 50 theoretical trays;

b) providing a second separation column, a second overhead condenser, and a second reboiler, the second separtion column defining a second separation zone having an upper portion, a lower portion and an intermediate portion, the intermediate portion of the second separation zone comprising at least about 9 theoretical trays;

c) introducing a hydrocarbon feedstock comprising DCPD to the intermediate portion of the first separation zone;

d) allowing a first vaporous overhead stream comprising $C_9$-hydrocarbons, and having a pressure in the range of from about 0.5 psia to about 3.0 psia and a temperature in the range of from about 160° F. to about 200° F., to pass from the upper portion of the first separation column to the first overhead condenser;

e) condensing at least a portion of the first vaporous overhead stream in the first overhead condenser thereby forming a first condensate having a temperature in the range of from about 50° F. to about 90° F.;

f) refluxing at least a portion of the first condensate from the first overhead condenser to the upper portion of the first separation zone;

g) allowing a first liquid bottoms stream comprising $C_{10}+$ hydrocarbons to pass from the lower portion of the first separation column to the first reboiler;

h) reboiling at least a portion of the first liquid bottoms stream in the first reboiler at a temperature in the range of from about 210° F. to about 250° F. thereby forming a first reboiled stream and a remaining portion of the first liquid bottoms stream;

i) introducing the first reboiled stream to the lower portion of the first separation zone;

j) introducing the remaining portion of the first liquid bottoms stream to the intermediate portion of the second separation zone;

k) allowing a second vaporous overhead stream comprising DCPD, and having a pressure in the range of from about 0.1 psia to about 2.0 psia and a temperature in the range of from about 160° F. to about 200° F., to pass from the upper portion of the second separation zone to the second overhead condenser;

l) condensing at least a portion of the second vaporous overhead stream in the second overhead condenser thereby forming a second condensate having a temperature in the range of from about 70° F. to about 100° F.;

m) refluxing at least a portion of the second condensate to the upper portion of the second separation zone and thereby forming a remaining portion of the second condensate;

n) allowing a second liquid bottoms stream comprising fuel oil to pass from the lower portion of the second separation zone to the second reboiler;

o) reboiling at least a portion of the second liquid bottoms stream in the second reboiler at a temperature in the range of from about 190° F. to about 240° F. thereby forming a second reboiled stream;

p) introducing the second reboiled stream to the lower portion of the second separation zone; and q) recovering the remaining portion of the second condensate from the second overhead condenser thereby forming a DCPD stream.

Other objects and advantages will become apparent from the detailed description and the appended claims.

DETAILED DESCRIPTION OF THE INVENTION

The process of this invention involves the upgrading of a hydrocarbon feedstock comprising CPD, DCPD, $C_5$ diolefins, benzene, toluene, and xylene.

The hydrocarbon feedstock generally comprises hydrocarbons having greater than 4 carbon atoms per molecule. The hydrocarbon feedstock can be a pyrolysis gasoline from a thermal hydrocarbon (such as ethane, propane and naphtha) cracking process. The hydrocarbon feedstock can also be a pyrolysis gasoline which has been debutanized, and is generally referred to as DAC.

The hydrocarbon feedstock typically contains in the range of from about 1.0 wt. % to about 20 wt. % CPD, more typically from about 1.0 wt. % to about 15 wt. % CPD, and most typically from 1.5 wt. % to 10 wt. % CPD, based on the total weight of the hydrocarbon feedstock; and, typically contains in the range of from about 0.5 wt. % to about 50 wt. % DCPD, more typically from about 1.0 wt. % to about 40 wt. % DCPD, and most typically from 1.5 wt. % to 30 wt. % DCPD, based on the total weight of the hydrocarbon feedstock In accordance with the first embodiment of the invention, the hydrocarbon feedstock is heated in a heating zone in such a manner as to provide the dimerization of at least a portion of the CPD contained in the hydrocarbon feedstock to DCPD, thereby forming a first effluent. More particularly, the heating in the heating zone is conducted at a temperature in the range of from about 100° F. to about 450° F., preferably from about 200° F. to about 400° F.; and most preferably from 200° F. to 300° F. The wt. % of CPD in the first effluent is preferably less than about 2 wt. %, more preferably less than about 1.5 wt. %, and most preferably less than 1 wt. %, based on the total weight of the first effluent.

The first effluent can then be separated, by any means, such as distillation, into a $C_6+$ stream comprising hydrocarbons having greater than 5 carbon atoms per molecule, and a $C_5$ diolefin stream comprising $C_5$ diolefins, such as, but not limited to, isoprene and cis and trans 1,3 pentadiene (piperylene).

The $C_6+$ stream can be separated, by any suitable means, such as distillation, into a $C_6-C_9$ stream comprising hydrocarbons having in the range of from and including 6 to and including 9 carbon atoms per molecule and into a $C_{10}+$ stream comprising hydrocarbons having greater than 9 carbon atoms per molecule.

The $C_6-C_9$ stream typically contains sulfur in the range of from about 10 to about 200 ppmw, more typically in the range of from about 10 to about 100 ppmw, and most typically from 10 to 50 ppmw, based on the total weight of the $C_6-C_9$ stream. The $C_6-C_9$ stream also typically has a bromine number in the range of from about 10 to about 100, more typically from about 10 to about 50, and most typically from 10 to 30 grams of bromine/100 grams of sample. The bromine number, as referred to herein, is determined using ASTM test method D1492-96 and is an indicator of the amount of olefins contained in a hydrocarbon stream. A low bromime number indicates low levels of olefins.

The $C_{10}+$ stream can be separated, by any suitable means, such as distillation, into a fuel oil stream comprising hydrocarbons having greater than 10 carbon atoms per molecule, and into a DCPD stream comprising DCPD.

The $C_6-C_9$ stream can be hydrotreated, by any suitable means for hydrotreating hydrocarbons, to thereby form a BTX stream comprising benzene, toluene and xylene. More particularly, the hydrotreating can be accomplished by contacting the $C_6-C_9$ stream with a hydrogenation catalyst, in a first reaction zone and in the presence of hydrogen, to hydrogenate at least a portion of the olefins, diolefins, alkynes, and styrene contained in the $C_6-C_9$ stream, thereby forming a second effluent having a lower bromine number than the $C_6-C_9$ stream.

The first reaction zone can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The hydrogenation catalyst can be any composition effective for hydrogenating unsaturated hydrocarbons. More particularly, the hydrogenation catalyst can comprise, consist of, or consist essentially of a Group VIII metal selected from the group consisting of iron, cobalt, nickel, ruthenium, rhodium, palladium, osmium, iridium, platinum and combinations of any two or more thereof. Preferably, the hydrogenation catalyst comprises palladium.

The hydrogenation in the first reaction zone is preferably carried out under reaction conditions effective for hydrogenating unsaturated hydrocarbons. The reaction temperature is more particularly in the range of from about 100° F. to about 600° F., preferably from about 150° F. to about 400° F., and most preferably from 150° F. to 370° F. The contacting pressure can range from about 15 psia to about 1000 psia, preferably from about 50 psia to about 500 psia, and most preferably from 150 psia to 500 psia. The WHSV can be in the range of from about 0.1 hr.$^{-1}$ to about 40 hr.$^{-1}$, preferably from about 0.25 hr.$^{-1}$ to about 20 hr.$^{-1}$, and most preferably from 1.0 hr.$^{-1}$ to 10 hr.$^{-1}$. The hydrogen to hydrocarbon ratio can be in the range of from about 10 to about 5000 standard cubic feet of hydrogen per barrel of hydrocarbon, preferably from about 20 to about 2500, and most preferably from 100 to 1000.

The second effluent can be contacted with a hydrodesulfurization catalyst, in a second reaction zone and in the presence of hydrogen, to desulfurize at least a portion of the sulfur-containing compounds contained in the second effluent, and to saturate substantially most of the olefinic and diolefinic compounds contained in the second effluent, thereby forming the BTX stream. The BTX stream preferably contains less than about 2 ppmw, more preferably less than about 1.5 ppmw, and most preferably less than 1.0 ppmw sulfur, based on the total weight of the BTX stream. The BTX stream also preferably has a bromine number in the range of from about 0 to about 2, preferably from about 0 to about 1, and most preferably from 0 to 0.5.

The second reaction zone can be operated as a batch process step or, preferably, as a continuous process step. In the latter operation, a solid catalyst bed or a moving catalyst bed or a fluidized catalyst bed can be employed Any of these operational modes have advantages and disadvantages, and those skilled in the art can select the one most suitable for a particular feed and catalyst.

The hydrodesulfurization catalyst can be any composition effective for desulfurizing sulfur containing hydrocarbon feedstocks. More particularly, the hydrodesulfurization catalyst can comprise, consist of, or consist essentially of a Group VIII metal selected from the group consisting of iron, cobalt, nickel, ruthenium rhodium, palladium, osmium, iridium, platinum, and combinations of any two or more thereof, and a Group VIB metal selected from the group consisting of chromium, molybdenum, tungsten, and combinations of any two or more thereof. Preferably, the hydrodesulfurization catalyst comprises nickel and molybdenum.

The hydrodesulfurization in the second reaction zone is preferably carried out under reaction conditions effective for reducing the sulfur content of sulfur-containing hydrocarbons and effective for saturating olefinic hydrocarbons. The reaction temperature is more particularly in the range of from about 300° F. to about 800° F.; preferably from about 400° F. to about 700° F.; and most preferably from 500° F. to 650° F. The contacting pressure can range from about 15 psia to about 1000 psia, preferably from about 50 psia to about 500 psia, and most preferably from 150 psia to 500 psia The WHSV can be in the range of from about 0.1 hr.$^{-1}$ to about 40 hr.$^{-1}$, preferably from about 0.25 hr.$^{-1}$ to about 20 hr.$^{-1}$, and most preferably from 1.0 hr.$^{-1}$ to 10 hr.$^{-1}$. The hydrogen to hydrocarbon ratio can be in the range of from about 10 to about 5000 standard cubic feet of hydrogen per barrel of hydrocarbon, preferably from about 20 to about 2500, and most preferably from 100 to 1000.

In accordance with the second embodiment of the invention, the hydrocarbon feedstock, as described above, is heated in a heating zone in such a manner as to provide the dimerization of at least a portion of the CPD contained in the hydrocarbon feedstock to DCPD, thereby forming a first effluent. More particularly, the heating in the heating zone is conducted at a temperature in the range of from about 100° F. to about 450° F., preferably from about 200° F. to about 400° F., and most preferably from about 200° F. to 300° F. The wt. % of CPD in the first effluent is preferably less than about 2 wt. %, more preferably less than about 1.5 wt. %, and most preferably less than 1 wt. %, based on the total weight of the first effluent.

The first effluent can then be separated, by any means, such as distillation, into a $C_{10}$+stream comprising hydrocarbons having greater than 9 carbon atoms per molecule, and a $C_5$–$C_9$ stream comprising hydrocarbons having in the range of from and including 5 to and including 9 carbon atoms per molecule.

The $C_5$–$C_9$ stream typically contains sulfur in the range of from about 10 ppmw to about 200 ppmw, more typically from about 10 ppmw to 100 ppmw, and most typically from 10 to 50 ppmw, based on the total weight of the $C_5$–$C_9$ stream. The $C_5$–$C_9$ stream also typically has a bromine number in the range of from about 10 to about 200, more typically from about 10 to about 100, and most typically from 10 to 60.

The $C_{10}$+stream can be separated, by any suitable means, such as distillation, into a fuel oil stream comprising hydrocarbons having greater than 10 carbon atoms per molecule, and into a DCPD stream.

The $C_5$–$C_5$ stream can be contacted with a selective hydrogenation catalyst, in a first reaction zone and in the presence of hydrogen, to hydrogenate at least a portion of the diolefins, alkynes, and styrene contained in the $C_5$–$C_9$ stream, thereby forming a second effluent having a lower bromine number than the $C_5$–$C_9$ stream.

The first reaction zone can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The selective hydrogenation catalyst can be any composition effective for selectively hydrogenating $C_5$ diolefins to $C_5$ olefins. More particularly, the selective hydrogenation catalyst can comprise, consist of, or consist essentially of a first component comprising a palladium-containing material selected from the group consisting of palladium metal, palladium oxides, and combinations of any two or more thereof; and a second component selected from the group consisting of silver, or an alkali-metal halide. When the second component is silver, the catalyst can be further promoted with an alkali-metal fluoride. Suitable selective hydrogenation catalysts, and methods of making such, are disclosed in U.S. Pat. No. 5,866,735, and in U.S. Pat. No. 5,510,550, which are each incorporated herein by reference. Preferably, the selective hydrogenation catalyst comprises palladium, silver and potassium fluoride or palladium and potassium iodide. Alkali-metal, as used herein, includes lithium, sodium, potassium, rubidium, cesium and francium.

The hydrogenation in the first reaction zone is preferably carried out under reaction conditions effective for hydrogenating unsaturated hydrocarbons. The reaction temperature is more particularly in the range of from about 100° F. to about 600° F., preferably from about 150° F. to about 400° F., and most preferably from 150° F. to 370° F. The contacting pressure can range from about 15 psia to about 1000 psia, preferably from about 50 psia to about 500 psia, and most preferably from 150 psia to 500 psia. The WHSV can be in the range of from about 0.1 hr.$^{-1}$ to about 40 hr.$^{-1}$, preferably from about 0.25 hr.$^{-1}$ to about 20 hr.$^{-1}$, and most preferably from 1.0 hr.$^{-1}$ to 10 hr.$^{-1}$. The hydrogen to hydrocarbon ratio can be in the range of from about 10 to about 5000 standard cubic feet of hydrogen per barrel of hydrocarbon, preferably from about 20 to about 2500, and most preferably from 100 to 1000.

The second effluent can be separated, by any suitable means, such as distillation, into a $C_6$–$C_9$ stream comprising hydrocarbons having in the range of from and including 6 to and including 9 carbon atoms per molecule and into a $C_5$ olefin stream comprising $C_5$ olefins.

The $C_6$–$C_9$ stream can be contacted with a hydrodesulfurization catalyst, as described in the first embodiment, in a second reaction zone and in the presence of hydrogen, to desulfurize at least a portion of the sulfur-containing compounds contained in the $C_6$–$C_9$ stream, and to saturate substantially most of the olefinic and diolefinic compounds contained in the $C_6$–$C_9$ stream, thereby forming a BTX stream comprising benzene, toluene and xylene. The BTX stream preferably contains less than about 2 ppmw, more preferably less than about 1.5 ppmw, and most preferably less than about 1.0 ppmw sulfur, based on the total weight of the BTX stream. The BTX stream also preferably has a bromine number in the range of from about 0 to about 2, more preferably from about 0 to about 1, and most preferably from 0 to 0.5.

The second reaction zone can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The hydrodesulfurization in the second reaction zone is preferably carried out under reaction conditions effective for reducing the sulfur content of sulfur-containing hydrocarbons and effective for saturating olefinic hydrocarbons. The reaction temperature is more particularly in the range of from about 300° F. to about 800° F.; preferably from about 400° F. to about 700° F.; and most preferably from 500° F. to 650° F. The contacting pressure can range from about 15 psia to about 1000 psia, preferably from about 50 psia to about 500 psia, and most preferably from 150 psia to 500 psia. The WHSV can be in the range of from about 0.1 hr.$^{-1}$ to about 40 hr.$^{-1}$, preferably from about 0.25 hr.$^{-1}$ to about 20 hr.$^{-1}$, and most preferably from 1 hr.$^{-1}$ to 10 hr$^{-1}$. The hydrogen to hydrocarbon ratio can be in the range of from about 10 to about 5000 standard cubic feet of hydrogen per barrel of hydrocarbon, preferably from about 20 to about 2500, and most preferably from 100 to 1000.

In accordance with the third embodiment of the invention, DCPD can be recovered from a hydrocarbon feedstock comprising DCPD. The hydrocarbon feedstock can be the $C_6$+stream from the first embodiment, or the first effluent from the second embodiment, or any hydrocarbon stream comprising DCPD including, but not limited to, pyrolysis gasoline as described above.

A first separation column, a first overhead condenser, and a first reboiler are provided. The fist separation column defines a first separation zone having an upper portion, a lower portion, and an intermediate portion. The intermediate portion of the first separation zone comprises at least about 50 theoretical trays, preferably at least about 55 theoretical trays, and most preferably at least 60 theoretical trays.

A second separation column, a second overhead condenser, and a second reboiler are provided. The second separation column defines a second separation zone having an upper portion, a lower portion, and an intermediate portion. The intermediate portion of the second separation zone comprises at least about 9 theoretical trays, preferably at least about 10 theoretical trays, and most preferably at least 11 theoretical trays.

The hydrocarbon feedstock can be introduced to the intermediate portion of the first separation zone. The theoretical tray location where the hydrocarbon feedstock is introduced to the intermediate portion of the first separation zone can be in the range of from about 10 to about 30, preferably from about 10 to about 20, and most preferably from 15 to 20. A first vaporous overhead stream comprising $C_9$–hydrocarbons (hydrocarbons having less than 10 carbon atoms per molecule), and having a pressure in the range of from about 0.5 psia to about 3.0 psia, preferably from about 0.5 psia to about 2.0 psia, and most preferably from 1.0 psia to 1.5 psia and a temperature in the range of from about 160° F. to about 200° F., preferably from about 170° F. to about 200° F., and most preferably from 180° F. to 200° F., is allowed to pass from the upper portion of the first separation column to the first overhead condenser wherein at least a portion of the first vaporous overhead stream is condensed, thereby forming a first condensate. The first condensate has a temperature in the range of forming about 50° F. to about 90° F., more preferably from about 50° F. to about 80° F., and most preferably from 50° F. to 70° F.

At least a portion of the first condensate can be refluxed to the upper portion of the first separation zone at a reflux ratio in the range of from about 0.1 to about 1.0, preferably from about 0.2 to about 0.7, and most preferably from 0.3 to 0.5. Reflux ratio, as used herein, refers to the volume of condensate returned to the upper portion of a separation column divided by the remaining volume of condensate which is not returned to the separation column. The remaining portion of the first condensate (which is not refluxed) can be passed downstream for further processing. The remaining portion of the first condensate represents the $C_6$–$C_9$ stream in the first embodiment or the $C_5$–$C_9$ stream in the second embodiment.

A first liquid bottoms stream comprising $C_{10}$+ hydrocarbons is allowed to pass from the lower portion of the first separation column to the first reboiler wherein at least a portion of the first liquid bottoms stream is reboiled, thereby forming a first reboiled stream, at a temperature in the range of from about 210° F. to about 250° F., preferably from about 210° F. to about 240° F., and most preferably from 220° F. to 230° F.

The first reboiled stream can be introduced to the lower portion of the first separation zone. The remaining portion of the first liquid bottoms stream, which represents the $C_{10}$+ stream in both the first and second embodiments, can be introduced to the intermediate portion of the second separation zone. The theoretical tray location where the remaining portion of the first liquid bottoms stream is introduced to the intermediate portion of the second separation zone can be in the range of from about 2 to about 8, preferably from about 3 to about 7, and most preferably from 4 to 6.

A second vaporous overhead stream comprising DCPD, and having a pressure in the range of from about 0.1 psia to about 2.0 psia, preferably from about 0.2 psia to about 1.0 psia, and most preferably from 0.3 psia to 0.6 psia and a temperature in the range of from about 1 60° F. to about 200° F., preferably from about 1 80° F. to about 200° F., and most preferably from 190° F. to 200° F., is allowed to pass from the upper portion of the second separation column to the second overhead condenser wherein at least a portion of the second vaporous overhead stream is condensed, thereby forming a second condensate. The second condensate has a temperature in the range of from about 70° F. to about 100° F., preferably from about 80° F. to about 100° F., and more preferably from 90° F. to 100° F.

At least a portion of the second condensate can be refluxed to the upper portion of the second separation zone at a reflux ratio in the range of from about 0.1 to about 1.0, preferably from about 0.2 to about 0.7, and most preferably from 0.3 to 0.5. The remaining portion of the second condensate (which is not refluxed) can be passed downstream for further processing. The remaining portion of the second condensate represents the dicyclopentadiene stream in both the first and second embodiments.

A second liquid bottoms stream comprising fuel oil is allowed to pass from the lower portion of the second separation column to the second reboiler wherein at least a portion of the second liquid bottoms stream is reboiled, thereby forming a second reboiled stream, at a temperature in the range of from about 190° F. to about 240° F., preferably from about 190° F. to about 220° F., and most preferably from 190° F. to 210° F.

The second reboiled stream can be introduced to the lower portion of the second separation zone. The remaining portion of the second liquid bottoms stream represents the fuel oil stream in both the first and second embodiments.

The DCPD stream produced in the first, second, or third embodiment can comprise at least about 70 wt. % DCPD, preferably at least about 75 wt. % DCPD, and most preferably at least 80 wt. % DCPD, based on the total weight of the DCPD stream, and has a Pt-Co color which is less than about 30, preferably less than about 28, and most preferably less than 25. Pt-Co color, as used herein, is defined as the color of the liquid measured according to ASTM method D-1209.

In order to avoid the production of color bodies from the reaction of DCPD, and other hydrocarbon compounds, with oxygen or rust, the first separation column, first overhead condenser, first reboiler, second separation column, second overhead condenser, and second reboiler must be operated in the substantial absence of rust and oxygen. More particularly, it is preferred to operate the first separation column, first overhead condenser, first reboiler, second separation column, second overhead condenser, and second reboiler, and any ancillary equipment, in an air tight mode. Also, it is preferred to clean, either chemically or otherwise, the first separation column, first overhead condenser, first reboiler, second separation column, second overhead condenser, second reboiler, and any ancillary equipment, prior to their use in the inventive process to remove substantially all of the rust contained therein.

The following example is provided to further illustrate this invention and is not to be considered as unduly limiting the scope of this invention.

EXAMPLE

This example illustrates the upgrading of a pyrolysis gasoline stream using the inventive process as described above in the first and third embodiments.

A pyrolysis gasoline stream from a storage tank at a chemical plant was charged to a heating zone (a dimerizer) at an inlet temperature of about 246° F., and an outlet temperature of about 271° F., thereby forming a first effluent. The first effluent was then separated into a $C_5$ diolefin stream and a $C_6$+stream in a first separation column (depentanizer). The $C_6$+stream was then charged to a second separation column having a lower portion, an upper portion, and an intermediate portion containing structured packing, the intermediate portion having 58 theoretical trays. The point of introduction of the first effluent to the intermediate portion was at about the fifteenth theoretical tray. The first vaporous overhead stream in the upper portion of the second separation column was at a pressure of about 1.2 psia, and a temperature of 189° F. The overhead condenser for the second separation column condensed the first vaporous overhead stream to yield a condensate liquid with a temperature of about 55° F., and provided a reflux stream at a reflux ratio of about 0.30. The reboiler for the second separation column was operated at a temperature of about 227° F. A $C_6$–$C_9$ stream was removed from the condenser for the second separation column and a $C_{10}$+stream was removed from the reboiler for the second separation column. The $C_{10}$+stream was then charged to a third separation column having a lower portion, an upper portion, and an intermediate portion containing structured packing, the intermediate portion having 9 theoretical trays. The point of introduction of the $C_{10}$+stream to the intermediate portion was at about the sixth theoretical tray. The second vaporous overhead stream in the upper portion of the third separation column was at a pressure of about 1.6 psia, and a temperature of 189° F. The overhead condenser for the third separation column condensed the second vaporous overhead stream to yield a condensate liquid with a temperature of about 94° F., and provided a reflux stream with a reflux ratio of about 0.44. The reboiler for the third separation column was operated at a temperature of about 198.5° F. A DCPD stream was removed from the condenser for the third separation column and a fuel oil stream was removed from the reboiler for the third separation column.

The $C_6$–$C_9$ stream from the second separation column was combined with a prefractionated raw gasoline stream (prefrac gasoline) to form a combined stream, and the combined stream was contacted with a hydrogenation catalyst containing 0.75 wt. % palladium (obtained from Engelhard Corporation, Iselin, N.J. under product designation E347), in the presence of hydrogen, at a pressure of about 375 psia, in a reactor with an inlet temperature of about 166° F. The temperature differential across the reactor is controlled by recycling a portion of the effluent of the reactor, which has been cooled by a heat exchanger, to the middle portion of the reactor. The recycle rate is adjusted to maintain an outlet temperature of about 270° F. The partially hydrogenated combined stream at the outlet of the reactor constitutes a second effluent. The second effluent was contacted with a hydrodesulfurization catalyst comprising nickel and molybdenum (obtained from Akzo Nobel NV, Arnhem, NL under product designation KF840), in the presence of hydrogen, at a pressure of about 345 psia, an inlet temperature of about 550° F., and an outlet temperature of about 610° F., thereby producing a BTX stream. Compositional analyses of the pyrolysis gasoline stream, first effluent, $C_5$ diolefin stream, $C_6$–$C_9$ stream, prefrac gasoline, DCPD stream, combined stream, second effluent, and BTX stream, as analyzed by gas chromatography and normalized to sum to 100 wt. % or 100 Iv %, are presented in the table.

TABLE

| Component | Pyrol. gas. stream wt. % | First effluent wt. % | $C_8$ diolefin stream wt. % | $C_6$–$C_9$ stream wt. % | Prefrac. gas. wt. % | DCPD stream wt. % | Combined stream lv %[5] | Second effluent lv %[5] | BTX stream lv %[5] |
|---|---|---|---|---|---|---|---|---|---|
| Butadiene (BD) | 0.37 | 0.35 | 2.16 | — | — | — | — | — | — |
| $C_3$'s[1] | 0.20 | 0.19 | 1.25 | — | — | — | — | — | — |
| CPD | 3.70 | 0.86 | 5.15 | 0.10 | — | 0.18 | — | — | — |
| $C_3$'s[2] | 14.07 | 13.85 | 89.25[6] | — | 2.86 | — | 2.93[11] | 2.46[11] | 1.33[11] |
| Benzene | 46.18 | 45.58 | — | 79.68 | 39.63 | — | 65.17 | 64.90 | 63.96 |
| Toluene | 3.23 | 3.21 | — | 5.65 | 24.87 | — | 9.38 | 9.35 | 9.09 |
| Styrene | 0.96 | 0.36 | — | 1.77 | 13.08 | — | 4.83 | 0.06 | — |
| $C_6$–$C_9$[3] | 4.52[7] | 4.52[7] | 2.16 | 10.63 | 15.59[9] | 0.02 | 10.97 | 14.65 | 17.29 |
| DCPD | 17.75 | 20.20 | 0.03 | 1.84 | — | 83.72 | — | — | — |
| $C_{10}$+[4] | 9.02[7] | 10.88[7] | — | 0.33 | 3.97[10] | 16.08 | 6.72[10] | 8.58[10] | 8.33[10] |
| Total | 100.00 | 100.00 | 100.00 | 100.00 | 100.00 | 100.00 | 100.00 | 100.00 | 100.00 |
| Pt/Co Color | 100+[7] | 100+[7] | ND | 100+[7] | ND | 21 | ND | ND | ND |
| Bromine number[12] | ND[8] | ND | ND | ND | ND | ND | 28.4 | 10.9 | 0.58 |
| Total Sulfur, ppm wt. | ND | ND | ND | ND | ND | ND | 58.9 | ND | 0.3 |

[1]- excluding BD;
[2]- excluding CPD;
[3]- excluding benzene, toluene and styrene;
[4]- excluding CDPD;
[5]- IV % = liquid volume %;
[6]- breakdown of $C_3$'s in $C_3$ diolefin stream: pentanes and cyclopentane = 1.80 wt. %; pentenes = 38.80 wt. %; isoprene = 15.55 wt. %; piperylene = 28.99 wt. %; other $C_3$ diolefins = 4.07 wt. %; overall total $C_3$ diolefins = 87.41 wt. %;
[7]- estimated;
[8]- ND = not determined;
[9]- includes $C_6$–$C_9$ hydrocarbons excluding benzene, toluene and styrene;
[10]- includes $C_9$+ hydrocarbons;
[11]- includes $C_9$ and lighter hydrocarbons;
[12]- Grams of Br/100 grams of sample.

From the data in the Table, it is readily apparent that the process for upgrading a hydrocarbon feedstock comprising $C_5$ olefins, $C_5$ diolefins, CPD, DCPD and aromatics (BTX) results in the production of a purified DCPD stream (83.72 wt. % DCPD), a purified $C_5$ diolefin stream (87.41 wt.% $C_5$ diolefins), and a purified BTX stream (73.05 Iv % benzene and toluene).

Also, the DCPD stream produced by the inventive process has a Pt/Co color number of 21 which is well below 30, the typical specification for DCPD product streams.

Furthermore, the total sulfur of the BTX stream was 99.5% lower than the total sulfur of the combined stream, and, the bromine number of the BTX stream was 98.0% lower than the bromine number of the combined stream, indicating a much lower olefin concentration in the BTX stream.

Reasonable variations, modifications, and adaptations can be made within the scope of the disclosure and the appended claims without departing from the scope of this invention.

That which is claimed is:

1. A process for recovering DCPD from a hydrocarbon feedstock comprising the steps of:
   a) providing a first separation column, a first overhead condenser, and a first reboiler, said first separation column defining a first separation zone having an upper portion, a lower portion and an intermediate portion, said intermediate portion of said first separation zone comprising at least about 50 theoretical trays;
   b) providing a second separation column, a second overhead condenser, and a second reboiler, said second separation column defining a second separation zone having an upper portion, a lower portion and an intermediate portion, said intermediate portion of said second separation zone comprising at least about 9 theoretical trays;
   c) introducing a hydrocarbon feedstock comprising DCPD to said intermediate portion of said first separation zone;
   d) allowing a first vaporous overhead stream comprising $C_9$-hydrocarbons, and having a pressure in the range of from about 0.5 psia to about 3.0 psia and a temperature in the range of from about 160° F. to about 200° F., to pass from said upper portion of said first separation column to said first overhead condenser;
   e) condensing at least a portion of said first vaporous overhead stream in said first overhead condenser thereby forming a first condensate which has a temperature in the range of from about 50° F. to about 90° F.;
   f) refluxing at least a portion of said first condensate from said first overhead condenser to said upper portion of said first separation zone;
   g) allowing a first liquid bottoms stream comprising $C_{10}$+hydrocarbons to pass from said lower portion of said first separation column to said first reboiler;
   h) reboiling at least a portion of said first liquid bottoms stream in said first reboiler at a temperature in the range of from about 210° F. to about 250° F. thereby forming a first reboiled stream and a remaining portion of said first liquid bottoms stream;
   i) introducing said first reboiled stream to said lower portion of said first separation zone;
   j) introducing the remaining portion of said first liquid bottoms stream to said intermediate portion of said second separation zone;
   k) allowing a second vaporous overhead stream comprising DCPD, and having a pressure in the range of from about 0.1 psia to about 2.0 psia and a temperature in the range of from about 160° F. to about 200° F., to pass from said upper portion of said second separation zone to said second overhead condenser;
   l) condensing at least a portion of said second vaporous overhead stream in said second overhead condenser thereby forming a second condensate which has a temperature in the range of from about 80° F. to about 100° F.;

m) refluxing at least a portion of said second condensate to said upper portion of said second separation zone and thereby forming a remaining portion of said second condensate;

n) allowing a second liquid bottoms stream comprising fuel oil to pass from said lower portion of said second separation zone to said second reboiler;

o) reboiling at least a portion of said second liquid bottoms stream in said second reboiler at a temperature in the range of from about 190° F. to about 240° F. thereby forming a second reboiled stream;

p) introducing said second reboiled stream to said lower portion of said second separation zone; and q) recovering the remaining portion of said second condensate from said second overhead condenser thereby forming a DCPD stream.

2. A process in accordance with claim 1 wherein said intermediate portion of said first separation zone comprises at least about 55 theoretical trays, said pressure of said first vaporous overhead stream in step d) is in the range of from about 0.5 psia to about 2.0 psia, said temperature of said first vaporous overhead stream in step d) is in the range of from about 170° F. to about 200° F., said temperature in step h) is in the range of from about 210° F. to about 240° F., said intermediate portion of said second separation zone comprises at least about 10 theoretical trays, said pressure of said second vaporous overhead stream in step k) is in the range of from about 0.2 psia to about 1.0 psia, said temperature of said second vaporous overhead stream in step k) is in the range of from about 180° F. to about 200° F., and said temperature in step o) is in the range of from about 200° F. to about 220° F.

3. A process in accordance with claim 1 wherein said intermediate portion of said first separation zone comprises at least 60 theoretical trays, said pressure of said first vaporous overhead stream in step d) is in the range of from 1.0 psia to 1.5 psia, said temperature of said first vaporous overhead stream in step d) is in the range of from 180° F. to 200° F., said temperature in step h) is in the range of from 220° F. to 230° F., said intermediate portion of said second separation zone comprises at least 11 theoretical trays, said pressure of said second vaporous overhead stream in step k) is in the range of from 0.3 psia to 0.6 psia, said temperature of said second vaporous overhead stream in step k) is in the range of from 190° F. to 200° F., and said temperature in step o) is in the range of from 200° F. to 210° F.

4. A process in accordance with claim 1 wherein said hydrocarbon feedstock stream is introduced to said intermediate portion of said first separation zone at a theoretical tray location in the range of from about 10 to about 30.

5. A process in accordance with claim 1 wherein said hydrocarbon feedstock is introduced to said intermediate portion of said first separation zone at a theoretical tray location in the range of from about 10 to about 20.

6. A process in accordance with claim 1 wherein said hydrocarbon feedstock is introduced to said intermediate portion of said first separation zone at a theoretical tray location in the range of from 15 to 20.

7. A process in accordance with claim 1 wherein said remaining portion of said first liquid bottoms stream is introduced to said intermediate portion of said second separation zone at a theoretical tray location in the range of from about 2 to about 8.

8. A process in accordance with claim 1 wherein said remaining portion of said first liquid bottoms stream is introduced to said intermediate portion of said second separation zone at a theoretical tray location in the range of from about 3 to about 7.

9. A process in accordance with claim 1 wherein said remaining portion of said first liquid bottoms stream is introduced to said intermediate portion of said second separation zone at a theoretical tray location in the range of from 4 to 6.

10. A process in accordance with claim 1 wherein said at least a portion of said first condensate in step f) is refluxed to said upper portion of said first separation zone at a reflux ratio in the range of from about 0.1 to about 1.0.

11. A process in accordance with claim 1 wherein said at least a portion of said first condensate in step f) is refluxed to said upper portion of said first separation zone at a reflux ratio in the range of from about 0.2 to about 0.7.

12. A process in accordance with claim 1 wherein said at least a portion of said first condensate in step f) is refluxed to said upper portion of said first separation zone at a reflux ratio in the range of from 0.3 to 0.5.

13. A process in accordance with claim 1 wherein said at least a portion of said second condensate in step m) is refluxed to said upper portion of said second separation zone at a reflux ratio in the range of from about 0.1 to about 1.0.

14. A process in accordance with claim 1 wherein said at least a portion of said second condensate in step m) is refluxed to said upper portion of said second separation zone at a reflux ratio in the range of from about 0.2 to about 0.7.

15. A process in accordance with claim 1 wherein said at least a portion of said second condensate in step m) is refluxed to said upper portion of said second separation zone at a reflux ratio in the range of from 0.3 to 0.5.

16. A process in accordance with claim 1 wherein said first separation column, said first overhead condenser, said first reboiler, said second separation column, said second overhead condenser, and said second reboiler are operated in the substantial absence of rust and oxygen.

17. A process in accordance with claim 1 wherein substantially all of the rust contained in said first separation column, said first overhead condenser, said first reboiler, said second separation column, said second overhead condenser, and said second reboiler is removed prior to step c).

* * * * *